US011534138B2

(12) United States Patent
Sprung et al.

(10) Patent No.: US 11,534,138 B2
(45) Date of Patent: Dec. 27, 2022

(54) APPARATUS AND METHOD FOR DETERMINING MOTION OF AN ULTRASOUND PROBE

(71) Applicants: piur imaging GmbH, Vienna (AT); ImFusion GmbH, Munich (DE)

(72) Inventors: Julian Sprung, Munich (DE); Robert Bauer, Unterhaching (DE); Raphael Prevost, Munich (DE); Wolfgang Wein, Munich (DE)

(73) Assignees: piur imaging GmbH, Vienna (AT); ImFusion GmbH, Munich (DE)

( * ) Notice: Subject to any disclaimer, the term of this patent is extended or adjusted under 35 U.S.C. 154(b) by 391 days.

(21) Appl. No.: 16/644,388

(22) PCT Filed: Sep. 5, 2018

(86) PCT No.: PCT/EP2018/073875
§ 371 (c)(1),
(2) Date: Mar. 4, 2020

(87) PCT Pub. No.: WO2019/048482
PCT Pub. Date: Mar. 14, 2019

(65) Prior Publication Data
US 2020/0196984 A1    Jun. 25, 2020

(30) Foreign Application Priority Data

Sep. 7, 2017  (AT) .............................. A60088/2017

(51) Int. Cl.
*A61B 8/00*    (2006.01)
*G06T 7/10*    (2017.01)
(Continued)

(52) U.S. Cl.
CPC ............ *A61B 8/4254* (2013.01); *A61B 8/483* (2013.01); *A61B 8/58* (2013.01); *G06N 3/04* (2013.01);
(Continued)

(58) Field of Classification Search
CPC ......... A61B 8/5253; A61B 8/58; A61B 8/483; A61B 8/4254; G06T 7/20; G06T 7/10; G06N 3/08; G06N 3/04
See application file for complete search history.

(56) References Cited

U.S. PATENT DOCUMENTS

2003/0135115 A1*  7/2003  Burdette ................ A61N 5/103
                                                        600/437
2009/0093717 A1    4/2009  Carneiro et al.
(Continued)

FOREIGN PATENT DOCUMENTS

| EP | 2194506 A2 | 6/2010 | |
|---|---|---|---|
| EP | 3522789 B1 * | 11/2020 | ........... A61B 8/4245 |
| WO | 2017039663 A1 | 3/2017 | |

OTHER PUBLICATIONS

Prevost, R. "3D Freehand Ultrasound Without External Tracking Using Deep Learning" Medical Image Analysis 48 Feb. 8, 2018, pp. 1-16.*
(Continued)

*Primary Examiner* — Mia M Thomas
(74) *Attorney, Agent, or Firm* — Meunier Carlin & Curfman LLC

(57) ABSTRACT

A method of determining a three-dimensional motion of a movable ultrasound probe (10) is described. The method is carried out during acquisition of an ultrasound image of a volume portion (2) by the ultrasound probe. The method comprises receiving a stream of ultrasound image data (20) from the ultrasound probe (10) while the ultrasound probe is moved along the volume portion (2); inputting at least a
(Continued)

sub-set of the ultrasound image data (20, 40) representing a plurality of ultrasound image frames (22) into a machine-learning module (50), wherein the machine learning module (50) has been trained to determine the relative three-dimensional motion between ultrasound image frames (22); and determining, by the machine-learning module (50), a three-dimensional motion indicator (60) indicating the relative three-dimensional motion between the ultrasound image frames.

13 Claims, 5 Drawing Sheets

(51) Int. Cl.
*A61B 8/08* (2006.01)
*G06N 3/04* (2006.01)
*G06N 3/08* (2006.01)
*G06T 7/20* (2017.01)

(52) U.S. Cl.
CPC .............. *G06N 3/08* (2013.01); *G06T 7/10* (2017.01); *G06T 7/20* (2013.01); *A61B 8/5253* (2013.01); *G06T 2207/10016* (2013.01); *G06T 2207/10136* (2013.01); *G06T 2207/20081* (2013.01); *G06T 2207/20084* (2013.01)

(56) References Cited

U.S. PATENT DOCUMENTS

| | | | | |
|---|---|---|---|---|
| 2011/0184684 | A1* | 7/2011 | Li | A61B 90/36 702/94 |
| 2011/0301466 | A1 | 12/2011 | Yang et al. | |
| 2012/0101388 | A1* | 4/2012 | Tripathi | A61B 8/085 600/459 |
| 2012/0237913 | A1* | 9/2012 | Savitsky | A61B 8/58 434/262 |
| 2014/0100452 | A1* | 4/2014 | Jain | A61B 8/486 600/424 |
| 2015/0182191 | A1* | 7/2015 | Caluser | A61B 5/4312 600/407 |
| 2015/0201911 | A1* | 7/2015 | Halmann | A61B 10/04 600/424 |
| 2015/0238148 | A1 | 8/2015 | Georgescu et al. | |
| 2016/0093050 | A1 | 3/2016 | Bang et al. | |
| 2016/0113630 | A1 | 4/2016 | Chang et al. | |
| 2016/0113632 | A1* | 4/2016 | Ribes | A61B 8/5269 600/440 |
| 2018/0317881 | A1* | 11/2018 | Astigarraga | A61B 8/4263 |
| 2020/0037997 | A1* | 2/2020 | Viggen | A61B 8/0883 |
| 2020/0323514 | A1* | 10/2020 | Thienphrapa | A61B 8/5223 |
| 2021/0068782 | A1* | 3/2021 | Caluser | A61B 8/461 |
| 2021/0077063 | A1* | 3/2021 | Swisher | G06T 11/00 |
| 2021/0124422 | A1* | 4/2021 | Forsland | G10L 15/22 |
| 2021/0137416 | A1* | 5/2021 | Canfield | G16H 50/30 |
| 2022/0148199 | A1* | 5/2022 | Bauer | G06T 7/246 |

OTHER PUBLICATIONS

Prevost et al., "Deep Learning for Sensorless 3D Freehand Ultrasound Imaging", Sep. 4, 2017, Medical Image Computing and Computer-Assisted Intervention—MICCAI 2015: 18th International Conference. Munich, Germany, Oct. 5-9, 2015.

Rambach et al., "Learning to Fuse: A Deep Learning Approach to Visual-Inertial Camera Pose Estimation", 2016 EEE International Symposium on Mixed and Augmented Reality (Ismar), IEEE, Sep. 19, 2016, pp. 71-76.

Lang et al., "Fusion of electromagnetic tracking with speckle-tracked 3D freehand ultrasound using an unscented Kalman filter", Proceedings of SPIE, vol. 7265, Feb. 26, 2009, p. 72651A, 12 pages.

Miao, S., "Effective Image Registration for Motion Estimation in Medical Imaging Environments", Dissertation, University of British Columbia, 2016.

International Search Report and Written Opinion dated Oct. 24, 2018, for International Application No. PCT/EP2018/073875.

Office Action issued in AT Application No. A60088/2017 dated Aug. 10, 2018.

Communication under Rule 71(3) EPC Intent to Grant European Application No. 18765622.8 dated Dec. 17, 2019.

Decision to Grant in connection to European Application No. 18765622.8, dated Oct. 8, 2020.

* cited by examiner

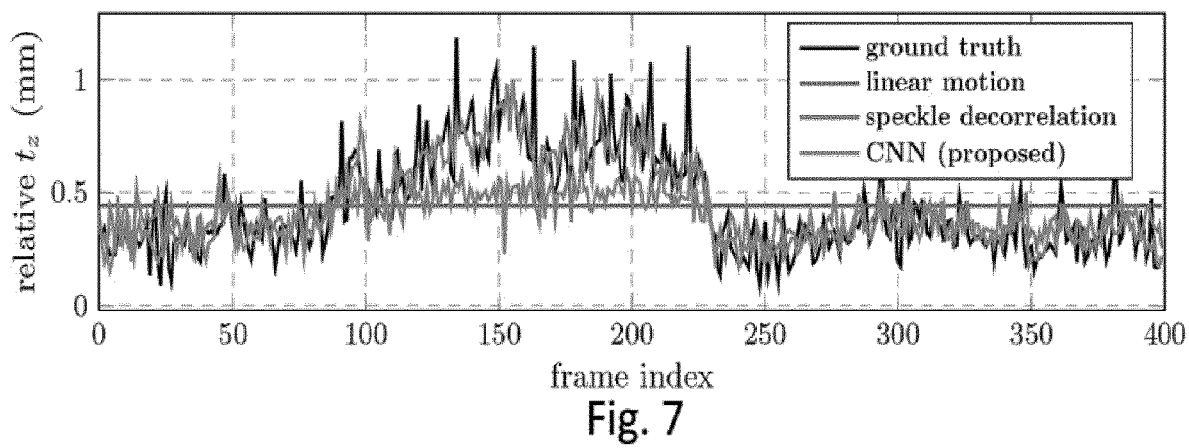
Fig. 7
Fig. 8a
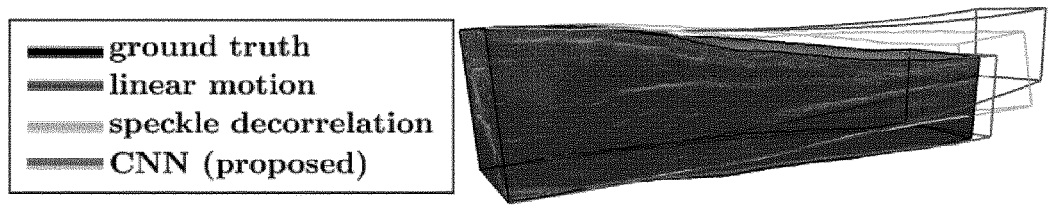
Fig. 8b
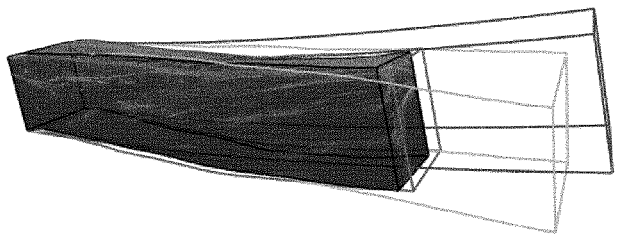
Fig. 8c
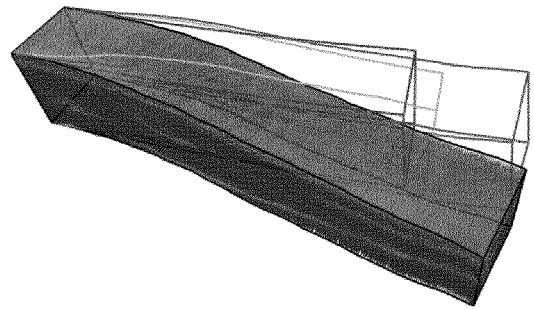

APPARATUS AND METHOD FOR DETERMINING MOTION OF AN ULTRASOUND PROBE

Aspects of the present application generally relate to a method of determining a three-dimensional motion of a movable ultrasound probe. The method is, in particular, carried out during acquisition of an ultrasound image of a volume portion by the ultrasound probe. The method comprises, in particular, the determining of a three-dimensional motion indicator indicating the relative three-dimensional motion between ultrasound image frames. Aspects of the present application also relate to a corresponding apparatus for determining a three-dimensional motion of an ultrasound probe.

TECHNICAL BACKGROUND

Ultrasound imaging (ultrasound) is one of the main medical modalities for both diagnostic and interventional applications thanks to its unique properties—affordability, availability, safety and real-time capabilities. For a long time, though, it has not been possible to acquire 3D images in a simple and reliable manner, and this limitation has reduced the range of clinical applications of ultrasound. The workaround was to acquire a series of 2D images by sweeping over the region of interest and combining them into a single volume afterwards.

One such implementation is, for example, described in WO 2015/191871 A1. This implementation requires a positioning system providing probe position information. External sensor-based solutions (typically using optical or electromagnetic tracking) are able to provide a good estimate of the ultrasound probe motion, and have therefore been primarily used. However, these solutions come at the expense of practicality and price.

Thus, research has been conducted for estimating the ultrasound probe motion, i.e., the relative position and orientation of the ultrasound probe from one image to the next, without additional hardware, by estimating the relative position of two images with pure image processing algorithms. It has been found that algorithms like "optical flow" allow estimating the in-plane motion quite reliably. However, estimating the out-of-plane motion (elevational displacement) remains a challenge.

One approach for estimating the out-of-plane motion, described for instance in U.S. Pat. No. 6,012,458, has been to exploit speckle noise patterns that are visible in ultrasound images, and is thus called "speckle decorrelation". "Speckle decorrelation" is based on the assumption that the elevational distance can be estimated by selecting and isolating speckles from the ultrasound images, and by comparing speckles of successive images: The higher the correlation between the speckles, the lower the elevational distance. However, one challenge remains the definition of the speckles and their correspondence across images. For these reasons, the existing "speckle decorrelation" method has been successfully applied only in rather specialized situations, and may not be successful in all real-life scenarios.

SUMMARY OF THE INVENTION

The present invention intends to overcome at least some of the above problems. The object is solved by the method, and by the apparatus claimed herein. Further advantages, features, aspects and details of the invention are evident from the dependent claims, the description and the drawings.

Thus, the method according to an aspect of the invention aims at bypassing the previous approaches, such as the speckle decorrelation model, which were based on pre-selected parts or features of ultrasound images. Instead, according to this aspect, the method provides an end-to-end solution with a fully machine learning-based approach, using image data representing entire ultrasound image frames as an input, without selection of any image portions or features.

Furthermore, aspects of the invention do not require any assumptions regarding the content of the image, such as the presence of speckles. Therefore, the method works with a broad range of application.

BRIEF DESCRIPTION OF FIGURES

The invention will be better understood by reference to the following description of embodiments of the invention taken in conjunction with the accompanying drawings, wherein:

FIG. 1b shows schematically a compounded three-dimensional ultrasound image obtained by the probe of FIG. 1a;

FIG. 2 shows schematically details of the method for acquiring the three-dimensional image illustrated in FIG. 1a;

FIG. 7 shows predictions of the elevational translation according to comparative examples and according to embodiments of the invention, respectively; and FIG. 8a-8c show 3D visualizations of tracked ultrasound sweeps according to comparative examples and according to embodiments of the invention, respectively.

DETAILED DESCRIPTION

Figure 1A:
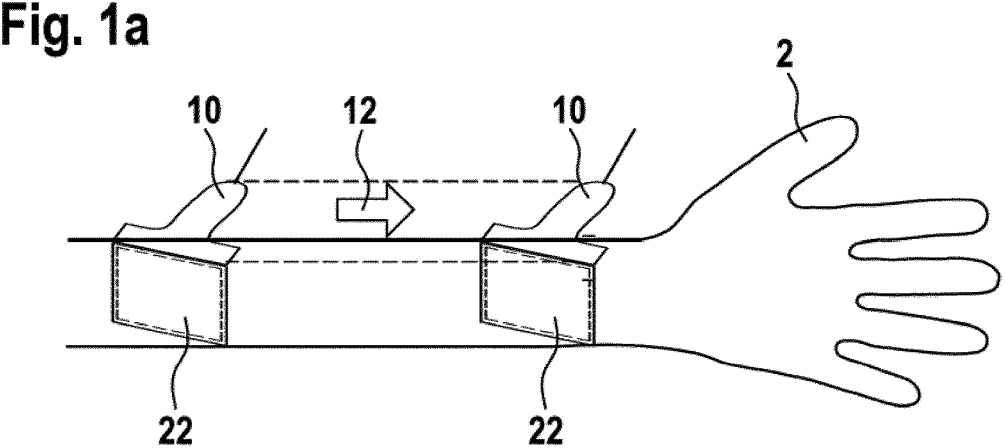
FIG. 1a shows schematically an ultrasound probe used in a method according to an embodiment of the invention.

FIG. 1a shows an ultrasound probe 10 being moved along a volume portion 2. Here, the volume portion 2 is a body portion of a patient. The motion of the probe is indicated by an arrow 12 representing the motion from a starting position (probe 10 shown on the left side of FIG. 1a) to a final position of motion (probe 10 shown on the right side of FIG. 1a). During the motion, the probe 10 collects ultrasound image data representing consecutive ultrasound image frames. Each ultrasound image frame provides an ultrasound image (i.e., graphically representable information of the ultrasound reflectivity properties) in a particular imaging region or image plane 22, i.e., in a two- or three-dimensional subspace of the volume portion 2. The imaging region 22 has a predetermined shape and location relative to the ultrasound probe 10, and the imaging region moves jointly with the ultrasound probe 10. By moving the ultrasound probe 10, the image region 22 is moved across the volume portion 2 so that the ultrasound image frames provide ultrasound images of various parts of the volume portion 2.

Here, an ultrasound image frame is defined as a two- or three-dimensional ultrasound image taken at a given time using the ultrasound probe. The image frame represents an entire image of a pre-defined size as acquired by the ultrasound probe. Subsequent image frames usually have the same resolution. In contrast, a dynamically selected subset of an ultrasound image frame, selected in dependence of the image content and possibly with variable size, is not an image frame. Typically, a time stamp is associated with the ultrasound image frame. The probe 10 collects the ultrasound image data as a data stream representing consecutive ultrasound image frames.

Figure 1B:
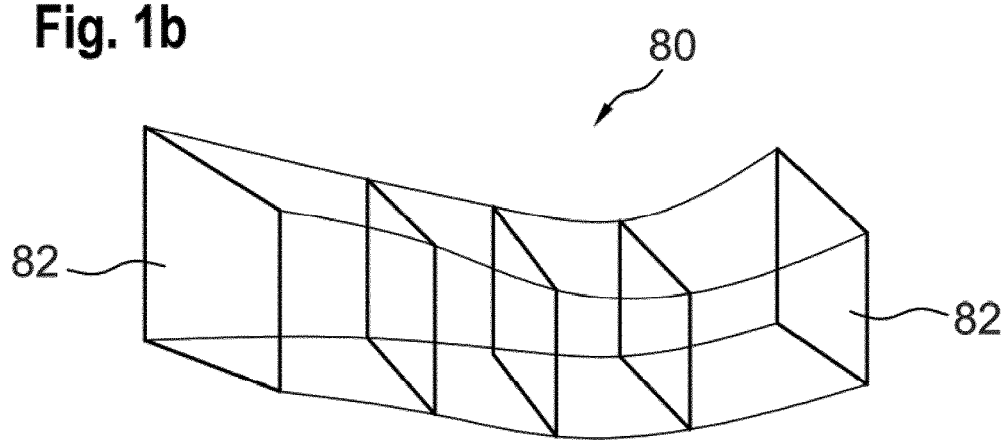

FIG. 1b shows the output of the proposed invention, a compounded three-dimensional ultrasound image. The compounded three-dimensional ultrasound image is a three-dimensional image indicating the ultrasound reflectivity properties in the scanned volume portion, obtained from the acquired ultrasound image frames and the determined movement (position and orientation) of the ultrasound probe 10 for each of the acquired ultrasound image frames 22. The compounded three-dimensional ultrasound image can, for example, be visualized as the set of the images frames positioned in space, or as a full 3D image, if further processed with a compounding algorithm such as the 3D reconstruction described further below.

Figure 2:
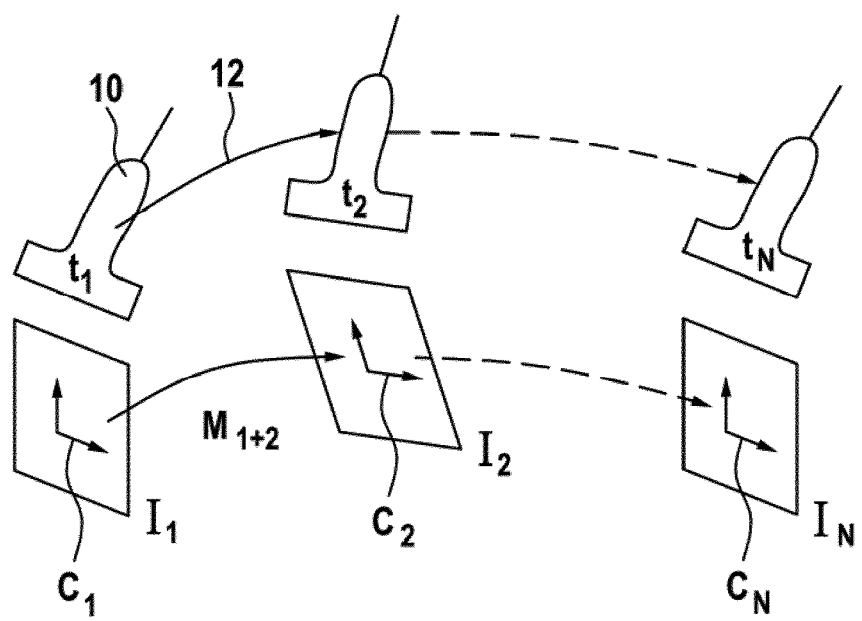

FIG. 2 depicts in more detail the challenging technical problem that the invention aims at solving. During the acquisition, the ultrasound probe (10) is moved and the image content of the image frames 22 is therefore changing. An object of the present invention is to recover the motion of the probe 12 between two instants t1 and t2, using solely information from the image data I1 and I2 acquired at such times. The estimated motion can be represented as a matrix M12 that models the relative transformation between the coordinate system of one frame C1 and the coordinate system of the other frame C2. This process can then be repeated for the whole series of images.

Typically, the motion has six degrees of freedom (three translations and three rotations), and the matrix M12 can be parametrized by 6 parameters.

Figure 3B:
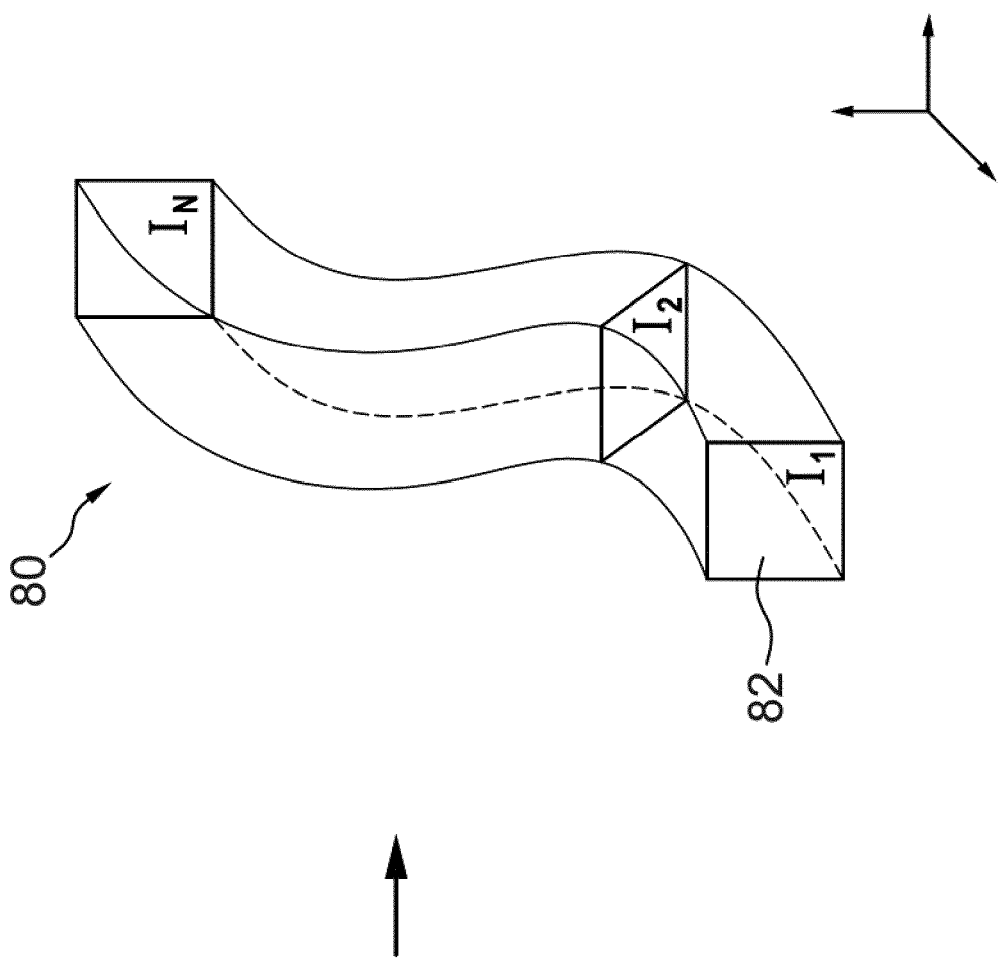
FIG. 3b shows schematically a compounded three-dimensional ultrasound image obtained by the method illustrated in FIG. 2
Figure 3A:
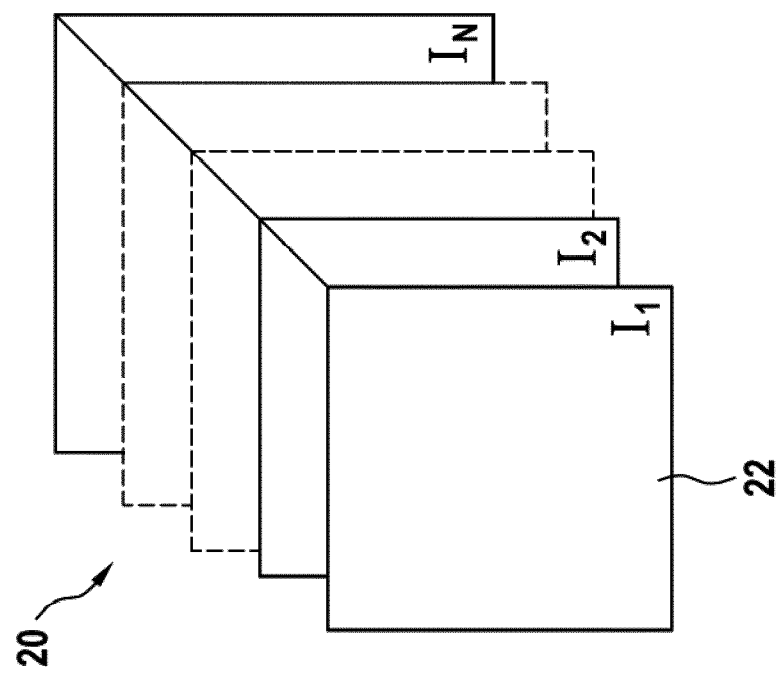
FIG. 3a shows schematically image data representing a plurality of ultrasound image frames, used as input in the method illustrated in FIG. 2.

FIG. 3a represents the input to the machine learning model 50, namely the ultrasound data 20 comprising a time series of ultrasound image frame data representing the ultrasound image frames 22 and corresponding time information (e.g., a time stamp or time index). In addition, the ultrasound data 20 may also comprise metadata, e.g., indicating ultrasound settings and/or presets such as gain, frequency, and/or dynamic range of the ultrasound image frames 22. The metadata may partially or fully be provided as a time series as well. In addition, the input to the machine learning model 50 may optionally include sensor data 24, e.g., a time series of sensor data and corresponding time information, as described in more detail with respect to FIG. 4.

FIG. 3b corresponds to FIG. 1b and the description of FIG. 1b is also applicable to FIG. 3b.

Figure 4:
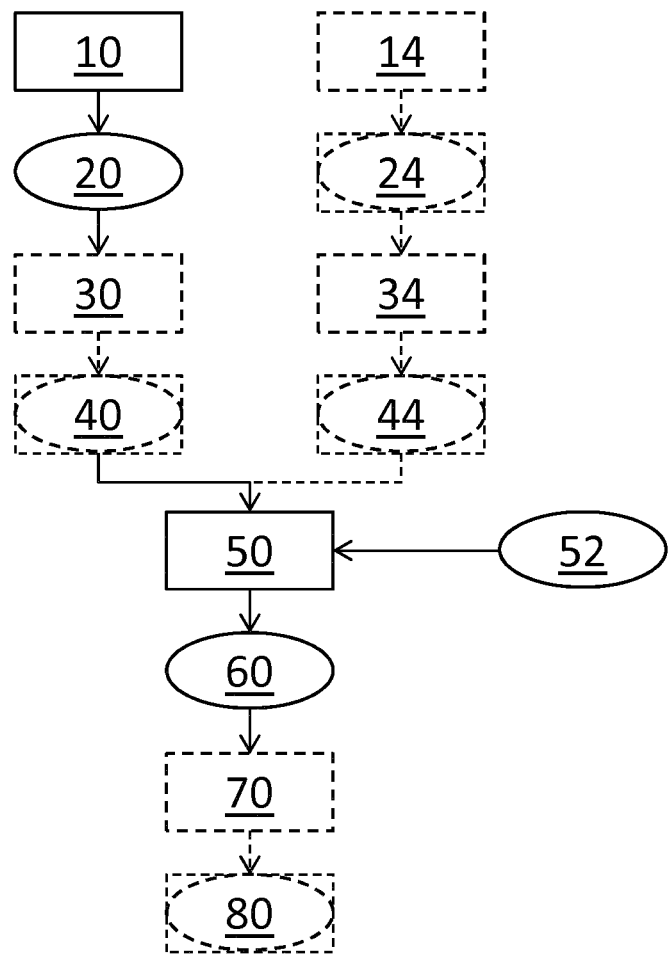
FIG. 4 shows schematically an apparatus for determining a three-dimensional motion of an ultrasound probe according to an embodiment of the invention.

FIG. 4 shows the overall workflow of the proposed invention. Therein, optional steps are indicated with dashed lines. The main input of the system is the image data 20 generated by the ultrasound system 11 from the probe 10. Such images may be pre-processed with a variety of algorithms 30 like image resampling, image filtering or other high-level analysis. The pre-processed data 40 from multiple frames can then be input in a machine learning module 50 that is trained, from previous learning data 52, to produce an estimate 60 of the motion of the probe between the different input image frames. Such a process is repeated for all frames of the acquisition and the output of the machine learning model is then post-processed 70 to produce the final trajectory of the probe 80.

The training from previous learning data 52 is performed before its utilization and comprises adjusting the values of the model parameters so that its output values are as close as possible to the expected values, as is known in the art. In other words, the training comprises solving a minimization problem for minimizing a deviation functional (e.g., L2 norm) with respect to the expected values.

Optionally, when an external sensor 14 is mounted on the ultrasound probe, its data 24 can also be pre-processed 34 and be used as additional input 44 of the machine learning module 50. To this purpose the data 24 is synchronized with the image data 20, e.g., by use of time stamps.

Figure 5:
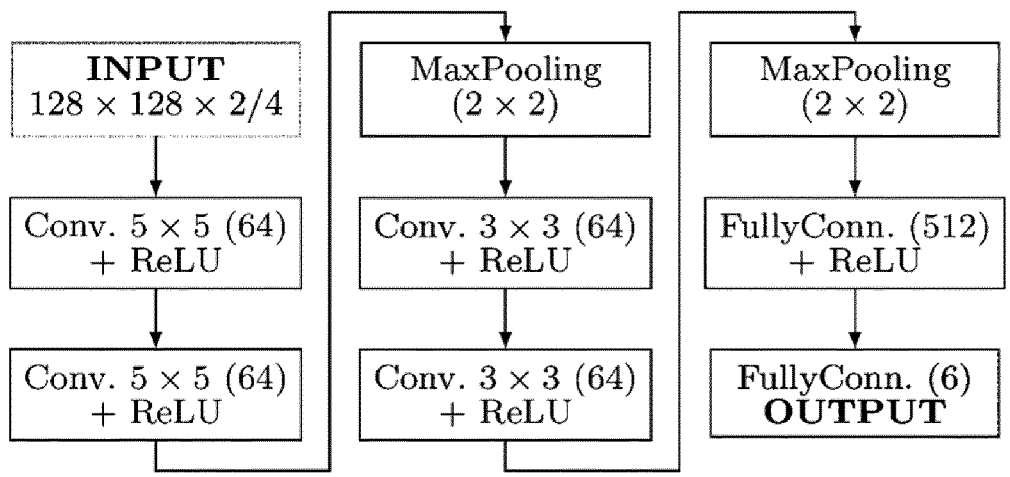
FIGS. 5 and 6 show schematically neural network architectures for a machine-learning module according to respective embodiments of the invention.

FIG. 5 represents an example of a machine learning module 50 for use in embodiments of the invention. The machine learning module 50 comprises a convolutional neural network. A two-channel image (representing two successive ultrasound frames) is the input of the neural network and goes through a series of convolutional layers (with 5×5 or 3×3 pixels kernels and 64 output channels), activation layers (here rectified linear units) and 2×2 pixels maximum pooling layers. At the end of the network, two fully connected layers aggregate the information from the whole features maps to a final output of six numbers representing 3 translations and 3 rotation parameters. These six numbers parametrize the matrix M12 mentioned above.

The parameters of the machine learning model (here the convolution kernels and the coefficients of the fully connected layers) are set as the final state of the training process. Given a set of training data (each training data sample can be composed of (i) a pair of successive ultrasound frames, and (ii) a very accurate estimate of the probe motion between those two frames, obtained for instance from a tracking system, and parameterized as six numbers), the training procedure can aim at minimizing the sum over all training data samples of the squared norm of the difference vector between the 6-dimensional output of the network and the 6 parameters of the actual measured probe motion. This minimization problem can be solved with a stochastic gradient descent or one of its variants like AdaGrad [John Duchi, Elad Hazan et Yoram Singer, «Adaptive subgradient methods for online learning and stochastic optimization», JMLR, vol. 12, 2011, p. 2121-2159] with a momentum of 90%, a batch size of 500 and no weight decay. The initial values of the network parameters can be randomly chosen, according to a Gaussian distribution with 0 mean and 0.01 standard deviation.

Optionally, an estimate of the in-plane translation can be pre-computed as the optical flow between the two images using known techniques (see article by Gunnar Farneback, cited further below). The output of this pre-computation of the optical flow is a 2D vector field that can be encoded as 2 additional optical flow channels. These 2 additional optical flow channels are used as additional input channels of the neural network (in addition to the 2 image channels described above).

Figure 6:
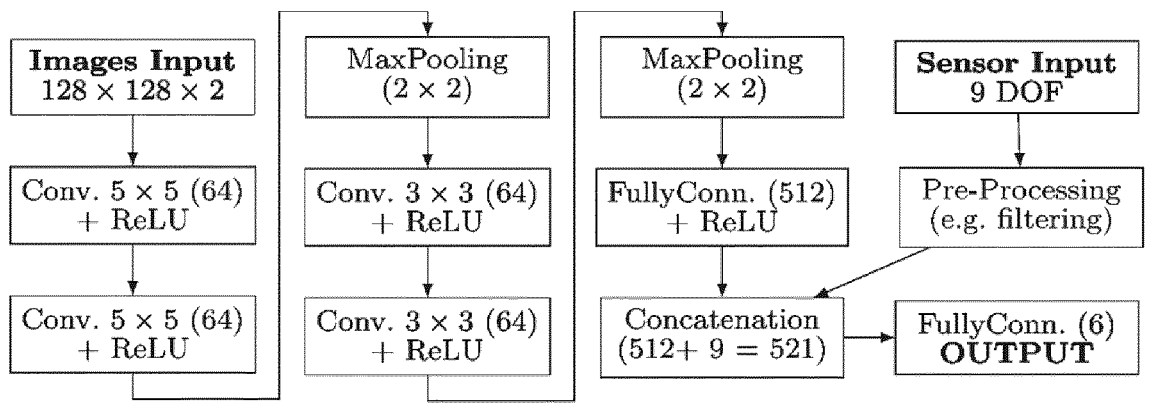

Similarly to FIG. 5, FIG. 6 represents an example of a neural network architecture that will take into account not only the image data but also some external IMU sensor information. The two architectures are mostly similar but the 9-dimensional measurements of the sensor are concatenated to the aggregated feature vector at the end of the network before producing the final output.

Next, test results of an example implementation according to an aspect of the invention, compared to prior art implementations, are discussed. For obtaining these test results, the set up described in the following was used.

Datasets acquisition and baseline methods: All sweeps used in the example implementations were captured with a Cicada-64 research ultrasound machine by Cephasonics (Santa Clara, Calif. USA). Therein, a linear 128-element probe was used. The probe was tuned at 9 MHz for generating the ultrasound images. The depth of all images was set to 5 cm (with a focus at 2 cm) and 256 scan-lines were captured per image.

The B-mode images were used without any filtering or back-scan conversion, resampled with an isotropic resolution of 0.3 mm. The probe was equipped with an optical target which was accurately tracked by the tracking system Stryker Navigation System III.

Using this tracking system, and after spatial and temporal image-to-sensor calibration, the inventors were able to obtain a ground truth transformation with absolute positioning accuracy of around 0.2 mm. It was also assured the temporal calibration exhibits neither jitter nor drift at all, thanks to the digital interface of the research US system and proper clock synchronization. Thus, the ground truth had sufficient precision from frame-to-frame.

The experiments were based on three datasets:
a set of 20 US sweeps (7168 frames in total) acquired on a BluePhantom ultrasound biopsy phantom. The images contain mostly speckle but also a variety of masses that are either hyperechoic or hypoechoic;
a set of 88 in-vivo tracked US sweeps (41869 frames in total) acquired on the forearms of 12 volunteers. Two different operators acquired at least three sweeps on both forearms of each participant;
another 12 in-vivo tracked sweeps (6647 frames in total) acquired on the lower legs on a subset of the volunteers. This last set was used to assess how the network generalizes to other anatomies.

All sweeps have been acquired in a fixed direction (proximal to distal). Applying the algorithm on a reversed sweep would yield a mirrored result. However, the method according to the present invention is not limited to any specific sweeping direction.

The algorithm according to the present invention was compared to two comparative methods:

linear motion, which is the expected motion of the operator in the sweeping direction.
This means all parameters are set to their average value over all acquisitions: rotations and in-plane translations are almost zero while elevational translation $t_z$ is constant around 2 cm/s;
speckle decorrelation method, according to the current state of the art: In this comparative method, each image was filtered to make the speckle pattern more visible as described in Afsham, N., Rasoulian, A., Najafi, M., Abolmaesumi, P., Rohling, R.: Nonlocal means filter-based speckle tracking. IEEE transactions on ultrasonics, ferroelectrics, and frequency control 62(8) (2015) 1501-1515. Then, each image was divided in 15×15 patches, and the corresponding patch-wise cross-correlations were computed. Then, a standard exponential-based model was computed to deduce the corresponding z-displacement from the correlation values. Finally RANSAC was used to compute a robust fit of the 6 transformation parameters to the displacement field. These method steps are described in Prager, R. W., Gee, A. H., Treece, G. M., Cash, C. J., Berman, L. H.: Sensorless freehand 3-d ultrasound using regression of the echo intensity. Ultrasound in medicine & biology 29(3) (2003) 437-446.

These comparative methods were compared to two implementations of embodiments of the present invention: The first implementation, referred to as "standard CNN" uses the convoluted neural network approach as described with reference to FIG. 5 above, with two input fields (two images between which the relative motion is to be determined). The second implementation, referred to as "CNN with optical flow", differs from the "standard CNN" in that it further uses the pre-computed optical flow, and therefore uses a total of four input fields as described with reference to FIG. 5 above.

For each of these methods and datasets, the three-dimensional motion indicators (three translations $t_x$, $t_y$, $t_z$, and three rotations $\theta_x$, $\theta_y$, $\theta_z$) were computed. Further, error metrics on these parameters were computed by comparing them with the data from the above-described tracking system. The parameter-wise errors were computed and averaged for every frame with respect to the first frame of the sweep. Further, a final drift, defined as the distance between the last image center with the estimated tracking and ground truth, was computed.

The results are summarized in the tables 1-3 below:

TABLE 1

| phantom dataset | avg. absolute error (mm/°) | | | | | | final drift (mm) | | |
| --- | --- | --- | --- | --- | --- | --- | --- | --- | --- |
| | $t_x$ | $t_y$ | $t_z$ | $\theta_x$ | $\theta_y$ | $\theta_z$ | min | med. | max |
| linear motion | 2.27 | 8.71 | 38.72 | 2.37 | 2.71 | 0.97 | 2.29 | 70.30 | 149.19 |
| speckle decorrelation | 4.96 | 2.21 | 29.89 | 2.10 | 1.46 | 1.93 | 12.67 | 47.27 | 134.93 |
| standard CNN | 2.25 | 5.67 | 14.37 | 2.13 | 1.86 | 0.98 | 14.31 | 26.17 | 65.10 |
| CNN with optical flow | 1.32 | 2.13 | 7.79 | 2.32 | 1.21 | 0.90 | 1.70 | 18.30 | 36.90 |

TABLE 2

| phantom dataset | avg. absolute error (mm/°) | | | | | | final drift (mm) | | |
| --- | --- | --- | --- | --- | --- | --- | --- | --- | --- |
| | $t_x$ | $t_y$ | $t_z$ | $\theta_x$ | $\theta_y$ | $\theta_z$ | min | med. | max |
| linear motion | 4.46 | 6.11 | 24.84 | 3.51 | 2.59 | 2.37 | 10.11 | 46.23 | 129.93 |
| speckle decorrelation | 4.36 | 4.09 | 18.78 | 2.53 | 3.02 | 5.23 | 9.19 | 36.36 | 98.95 |

TABLE 2-continued

| phantom dataset | avg. absolute error (mm/°) | | | | | | final drift (mm) | | |
|---|---|---|---|---|---|---|---|---|---|
| | $t_x$ | $t_y$ | $t_z$ | $\theta_x$ | $\theta_y$ | $\theta_z$ | min | med. | max |
| standard CNN | 6.30 | 5.97 | 6.15 | 2.82 | 2.78 | 2.40 | 3.72 | 25.16 | 63.26 |
| CNN with optical flow | 3.54 | 3.05 | 4.19 | 2.63 | 2.52 | 1.93 | 3.35 | 14.44 | 41.93 |
| after speckle filtering | 3.57 | 3.59 | 8.56 | 2.56 | 2.64 | 2.01 | 5.14 | 22.04 | 44.15 |

TABLE 3

| lower legs dataset | avg. absolute error (mm/°) | | | | | | final drift (mm) | | |
|---|---|---|---|---|---|---|---|---|---|
| | $t_x$ | $t_y$ | $t_z$ | $\theta_x$ | $\theta_y$ | $\theta_z$ | min | med. | max |
| linear motion | 4.49 | 4.84 | 39.81 | 4.39 | 2.18 | 2.46 | 37.35 | 73.40 | 143.42 |
| speckle decorrelation | 5.02 | 2.87 | 30.89 | 1.82 | 1.78 | 4.11 | 43.21 | 54.74 | 89.97 |
| standard CNN | 5.34 | 5.62 | 17.22 | 2.58 | 2.45 | 2.84 | 21.73 | 43.21 | 65.68 |
| CNN with optical flow | 4.14 | 3.91 | 17.12 | 1.94 | 2.58 | 2.15 | 25.79 | 40.56 | 52.72 |
| CNN trained on legs | 3.11 | 5.86 | 5.63 | 2.75 | 3.17 | 5.24 | 8.53 | 19.69 | 30.11 |

When comparing the above methods, it can be seen that the linear motion method gives the worst results of the four methods, mainly due to the out-of-plane translation $t_z$. This is expected since keeping a constant speed is difficult, so that this component is expected to have the largest variability. The speckle decorrelation method significantly reduces all estimation errors by exploiting the correlations between the frames; nevertheless the out-of-plane error on $t_z$ and therefore the overall drift is still quite high.

On the other hand, the standard CNN method (without optical flow channels) is able to produce results that are already better than the comparative examples. One can notice, however, that the $t_x$ and $t_y$ errors are somewhat high, especially on the forearm sweeps. This error may be reduced by additional training data allowing the system to learn the whole transformation more accurately by a larger dataset. This problem is also much reduced by adding the optical flow as input channels (CNN with optical flow method). Indeed, for the CNN with optical flow method, $t_x$ and $t_y$ for instance are estimated more accurately; and the estimation of $t_z$ is even further improved.

As a result, we observe on real clinical images a final drift of merely 1.45 cm over sequences longer than 20 cm, which is twice as accurate as the comparative examples. The hierarchy of the methods (from low to high accuracy: linear; speckle decorrelation; standard CNN; CNN with optical flow) was confirmed by paired signed-rank Wilcoxon tests which all yielded p-values lower than $10^{-6}$.

Next, the influence of noise filtering is discussed. In order to test the importance of the speckle noise, we compared the methods when applied on the images before and after applying the speckle filter built in the Cephasonics ultrasound system. As we can see in the last row of Table 2 above, learning and testing on the unfiltered images yields better tracking estimation. This shows that speckle patterns are important for the neural network, in particular for the estimation of the out of plane translation. On the other hand, the CNN methods on filtered images already give better results than the comparative methods. Thus, it can be concluded that speckle is indeed highly useful, but not strictly necessary for estimating out-of-plane motion.

Generalization to other anatomies: Another interesting question is how well the machine learning approach can generalize to other applications: does it really learn the motion from general statistics, or does it overfit to some anatomical structures present in the image?

The results are reported in Table 3 above. Here, the training data was based on a forearm dataset, but the results are reported for a lower leg dataset. Compared to Table 2, these results show a significant degradation of the accuracy for all methods. For the comparative methods, this is due to incorrect calibration (since they have been calibrated on the forearms dataset). For the methods according to the invention, the degradation is even more severe (since they have been learned on the forearms dataset). In more detail, the in-plane displacements are still recovered with a reasonable accuracy, but the error on the out-of-plane translation $t_z$ has strongly increased.

However, the methods according to the invention still generalize better than the others to new kind of images. This preliminary experiment shows that the accuracy is strongly dependent on the target anatomy but gives hope regarding the capabilities of machine-learning approaches.

For comparison, in the last row of Table 3, we also report the accuracy obtained with a CNN trained on this specific dataset, which is only slightly worse than on forearms (due to the smaller size of the dataset).

Next, FIG. 7 is discussed. Here, the same methods discussed above for Tables 1-3 have been used. For testing the out-of-plane estimation under challenging environments, the predictions by these methods is shown for a separate sweep with a deliberately strongly varying speed: The first 100 and last 150 frames were recorded at an average speed of 0.3 mm/frame, while inbetween the speed has almost been doubled. FIG. 7 shows the different predictions of the elevational translation.

As might be expected, the linear motion method assumes a constant speed and will therefore yield major reconstruction artifacts. The speckle decorrelation approach does detect a speed change but strongly underestimates large motions. Only the methods according to embodiments of the invention are able to follow the probe speed accurately.

A qualitative comparison of the reconstructed trajectories on a sample sweep is shown in FIGS. 8a-8c. Specifically, FIGS. 8a-8c show respective 3D visualizations of tracked ultrasound sweeps. The ultrasound frames have been displayed with their ground truth position and their trajectory are emphasized with the black contour. In comparison, the outline of the trajectories obtained with the other methods are also shown in other colors: red for the linear motion method, blue for our implementation of the speckle decorrelation method and green for our proposed method based on deep learning.

FIG. 8a represents a median case in terms of performance (more particularly final drift) for our method, FIG. 8b corresponds to the best case and FIG. 8c the worst case over the tested forearms dataset. They highlight the hierarchy of the different methods in terms of tracking estimation accuracy.

Further examples of test results of example implementations according to aspects of the invention can be found in the publication "3D freehand ultrasound without external tracking using deep learning", in: Medial Imaga Analysis (August 2018), Volume 48, Pages 187-202, retrieveable at http://doi.org/10.1016/j.media.2018.06.003, which is hereby incorporated in its entirety by reference.

Description of Further Aspects:

Next, various more general aspects of the invention are defined in more detail. Each aspect so defined may be combined with any other embodiment or with any other aspect(s) unless clearly indicated to the contrary. Reference signs referring to the Figures are for illustration only, but are not intended to limit the respective aspect(s) to the embodiments shown in the Figures.

According to an aspect, a three-dimensional motion of the ultrasound probe 10 is determined. According to an aspect, the three-dimensional motion has six degrees of freedom and includes a displacement (three degrees of freedom) and a rotation (three degrees of freedom). The displacement comprises in-plane displacements and elevational displacement; the rotation comprises in-plane rotation and out-of-plane rotations. Here, the terms in-plane and out-of-plane refer to an image plan defined by the image frame 22 acquired by the ultrasound probe 10. The three-dimensional motion indicator may be any parametrization of these degrees of freedom, or at least of a subset of these degrees of freedom. According to an aspect, the ultrasound probe is a free-hand probe and has the full six degrees of freedom. According to another aspect, the ultrasound probe is subject to constraints limiting the degrees of freedom to less than six.

The method includes receiving a stream of ultrasound image data from the ultrasound probe 10, and inputting at least a sub-set of the ultrasound image data representing a plurality of ultrasound image frames into a machine-learning module. The (sub-set of) ultrasound image data may be pre-processed, filtered or altered in any other manner. The term "at least a sub-set" requires that the information contained in the ultrasound image data from the ultrasound probe is at least partially input into the machine-learning module.

According to an aspect, even the full image data or a subset thereof is taken as the input subset. In case of a subset, the subset is taken irrespective of the image content of the ultrasound image frames and does therefore not require any image analysis.

Next, aspects relating to pre-processing of the ultrasound image data are described. According to an aspect, the method comprises pre-processing of the ultrasound image data before at least the subset of the ultrasound image data is input to the machine-learning module. For example, the pre-processing may include pre-computing a motion-indicative data. An example of motion-indicative data is the in-plane displacement data representing the in-plane displacement between the at least two of the ultrasound images.

The method may then comprise inputting the motion-indicative data (such as the in-plane displacement data) as an additional input to the machine learning module. For example, motion-indicative data may be a two-dimensional data set such as a vector field, and may be input to the machine learning module as an additional image channels.

An advantage of this aspect is that by inputting to the machine-learning module data representing explicitly some easily calculable aspects of the motion, the machine-learning module may be enabled to provide information on the remaining aspects more reliable and/or with fewer training data.

The pre-computing of the in-plane displacement may be carried out by any known method. According to an aspect, the pre-computing is carried out by an "optical flow" method such as the one described in [Gunnar Farneback, Two-frame motion estimation based on polynomial expansion, Lecture Notes in Computer Science, 2003, (2749), 363-370]. Thus, the in-plane displacement data may be computed as an optical flow vector field representing a sub-pixel dense optical flow between the at least two ultrasound images.

According to a further aspect, the ultrasound image data can be pre-processed using at least one of the following:

Resampling: The ultrasound image data may be resampled to a given size or such that each of its pixels has a given resolution. This is done to make the system robust to some settings of the ultrasound system (like the depth or the number of scanlines used).

Image Filtering: This includes any local filters (like low-pass or high-pass filters), adaptive filters (like speckle denoising, enhancing or masking) or global image transformation (like histogram equalization).

Segmentation: Another pre-processing would consist in segmenting the image, i.e. classifying all pixels as one of multiple classes and using such probability maps as additional inputs. In a medical application for instance, an example would be to segment the skin, the fat, the muscle and the bone pixels.

Any pre-computed feature: For instance, as described before, use as the optical flow vector field as additional channels for the model input According to a further aspect, if additional sensor data is input, the sensor data can be pre-processed using at least one of the above.

According to an alternative aspect, no pre-processing of the ultrasound image data takes place before at least the subset of the ultrasound image data is input to the machine-learning module.

Next, aspects relating to the machine learning module are described. According to an aspect, the machine learning module comprises a neural network. In particular, the machine learning module may comprise a convolutional neural network.

According to a further aspect, the convolutional neural network has a convolutional layer outputting a plurality of feature maps, each feature map being the result of a convolution with a particular kernel of the layer input. Throughout the present application, the indefinite article "a" is used in the sense of "at least one", and in particular includes the possibility of a plurality. The convolutional neural network may have a plurality of convolutional layers, e.g., two, three or four convolutional layers, connected to each other in series and optionally with a pooling layer between at least some of the convolutional layers.

According to a further aspect, the convolutional neural network also includes an activation layer (for instance a sigmoid or a rectified unit layer) and/or a fully connected layer that outputs either a global feature vector or the final prediction of the network. The convolutional neural network may, for example, comprise a plurality of (e.g. two) fully connected layers receiving input from the convolutional layer(s) and/or pooling layer(s), and providing as an output the motion data (e.g., six numbers representing 3 translations and 3 rotation parameters).

According to a further aspect, the neural network is a recurrent neural network having a dynamic temporal behavior (i.e. the prediction of the network for a given ultrasound image data depends on the previous frames that have been inputted in the network). One popular architecture choice is for instance the long short-term memories (LSTM) networks.

Although the machine learning module according to the invention has been mainly illustrated by a neural network, it is not limited to neural networks. Instead, other types of machine learning module may also be used. For example, according to a further aspect, the machine learning module may also include for example a random forest algorithm.

Next, aspects relating to further details of input data from the ultrasound probe are described.

According to an aspect, the method comprises inputting local image data corresponding to a pair (or subset) of (consecutive) image frames to the machine learning module for determining the relative three-dimensional motion between the pair (subset) of ultrasound image frames, and repeating this process for consecutive pairs or subsets of image frames.

According to an alternative aspect, the method comprises inputting a global set of image data substantially spanning the whole set of image frames to the machine learning module for determining the relative three-dimensional motion between a first one and a last one of the ultrasound image frames. Thus, for example the full stream of the ultrasound image data may be input into the machine-learning module.

According to a further aspect, the method may include skipping a frame such as each second frame. Thereby the demands on computing power may be reduced while still providing timely information.

According to a further aspect, the method may comprise inputting to the machine learning module a global set of image data substantially spanning the whole set of image frames. Then, the machine learning module may determine the relative three-dimensional motion between some ultrasound image frames such as a first one and a last one of the ultrasound image frames.

According to a further aspect, the image data is two- or three-dimensional, i.e. it describes two-dimensional image frames or a three-dimensional image frames. For example, three-dimensional image frames may be produced by using a probe capable of imaging small 3D ultrasound volumes, e.g. by a matrix array ultrasound transducer or by a wobbler ultrasound system.

According to a further aspect, the image data may include data obtained by at least one ultrasound imaging modes such as A-Mode, B-Mode, continuous harmonic imaging, color-Doppler mode, Plain wave imaging or the like. According to a further aspect, the image data may include raw radio frequency data. According to a further aspect, the image data is extracted from the ultrasound system at various points of the processing pipeline, for instance before the speckle noise filtering step.

According to a further aspect, the image data may include Doppler data which contains velocity information. The Doppler data may be obtained by an additional Doppler-capable ultrasound sensor.

According to a further aspect, the image data may include metadata indicating ultrasound settings, for examples presets such as gain, frequency, and/or dynamic range.

Next, aspects relating to the use of further (non-ultrasound) sensor data are described.

According to an aspect, an additional sensor may be provided (e.g., fixed to the ultrasound probe), and the method may include inputting sensor data from the additional sensor to the machine learning module. The above description of the image data may optionally also apply to the sensor data to the machine learning module.

For example, the additional sensor may comprise an acceleration sensor, the method comprises detecting an acceleration of the ultrasound probe by an acceleration sensor attached to the ultrasound probe; and inputting the acceleration corresponding to the at least two ultrasound image frames into the machine learning module. The acceleration data may be pre-processed, for example, for detecting abrupt motion which the machine learning module may be less able to handle, and for generating an abrupt-motion signal in case of detected abrupt motion.

Instead of or in addition to the data from an acceleration sensor, also any other sensor data may be used, in particular sensor data obtained from an IMU sensor such as acceleration, gyroscopic, magnetic field, barometric data, especially acceleration and/or gyroscopic.

According to a further aspect, the additional sensor may comprise a rotation sensor for detecting a rotation of the ultrasound probe.

According to a further aspect, the method may comprise tracking a position of the ultrasound probe (by a tracking system such as an optical tracking system, e.g., an inside-out tracker being stationary and tracking a marker set attached to the probe, or an outside-in tracker being attached to the probe and tracking a fixed marker set). The probe motion indicator may then be compared and/or combined with the tracking data to identify and/or compensate errors. Another mode of operation is to detect whether the tracking system fails (e.g., if the tracking marks are obstructed), and if the tracking system is determined to fail, using the determined probe motion indicator as a backup, by substituting the tracked position information from the tracking system by the probe position and orientation determined from the three-dimensional motion indicator (60). Thereby, the method according to this aspect may be used for making an existing tracking system more robust or precise.

According to a further aspect, the additional sensor comprises an optical device (for instance camera, or laser-based motion detecting system).

According to a further aspect, the method comprises generating, as a result of the comparison between the tracking data and the probe motion indicator, a reliability indicator of the probe motion indicator. For example, the method may comprise detecting an inconsistency between the determined three-dimensional motion and the sensor data, and in case of a detected inconsistency, generating an indication that the output is not reliable.

According to a further alternative aspect, no external tracker is provided.

Next, aspects relating to the ultrasound probe are described. According to an aspect, the ultrasound probe comprises an ultrasound transducer array for transmitting ultrasound beams and detecting ultrasound echoes reflected from an object volume of the volume portion at a multiplicity of sample volumes in a scan plane. According to a further aspect, the ultrasound image data is derived from ultrasound echoes reflected from each one of a multiplicity of scan planes through said body portion.

Next, aspects relating to the training data and the acquisition protocol are described.

According to an aspect, the machine learning module has been trained using a training image data stream being obtained using a pre-determined acquisition direction, and the method includes receiving the stream of ultrasound image data from the ultrasound probe while the ultrasound probe is moved along the body portion according to the pre-determined acquisition direction. Optionally, sensor data, synchronized.

According to a further aspect, the training data has been generated by using a separate tracking system which outputs the tracked position and/or motion of the probe for each image frame, and inputting an indicator of the tracked position and/or motion of the probe as a ground truth along with the training image data. Thus, according to an aspect, the training data includes (1) the ultrasound image data, (2) the tracking data as ground truth, and (3) optionally, the sensor data.

The training of the machine learning module can be implemented according to any know machine learning system. The machine learning module typically comprises a model function depending on model parameters (e.g., a neural network), wherein the input of the model function is the image data and other optional input of the machine learning module, and an output is the motion data as a function of the input and the parameters. Typically, the machine learning module is trained by solving an optimization problem for the model function using training data, i.e., input to the model function with known "true" output (ground truth, e.g., the known motion data coming from the accurate tracking system). The optimization problem consists in finding a set f model parameters minimizing a cost function, defined as an error measure between the output of the model function and the ground truth. One example of such an error measure is the squared L2 norm, i.e., the averaged squared difference between the 3 translation and 3 rotation parameters predicted by the model function of the machine learning module, and the ones computed from the tracking data.

Next, aspects relating to the further processing of the probe motion indicator are described. According to an aspect, the method comprises determining, from the probe motion indicator (from the relative three-dimensional displacement and rotation between the ultrasound image frames), a probe position and orientation of the ultrasound probe. The probe position and orientation may be obtained by discrete integration of multiple probe motion indicators.

According to a further aspect, the method comprises filtering of the determined probe position and orientation. For example, the method may comprise further refining and regularizing the probe motion indicator or the determined position and orientation of the probe, e.g., by comparing and/or averaging multiple estimates obtained by the machine learning module.

According to a further aspect, the method may comprise reconstructing a three-dimensional ultrasound image using the determined probe position and orientation and the stream of ultrasound image data, e.g., by any known 3D ultrasound volume compounding and/or reconstruction algorithm, see [Nicholas Rohling, Robert. (1999). 3D Freehand Ultrasound: Reconstruction and Spatial Compounding].

Next, some further aspects are described. According to an aspect, the volume portion is a body portion of a patient. For example, the body portion may include a limb portion such as a forearm portion and/or a leg portion of the patient, for example, for the clinical application of peripheral vein mapping for bypass surgery or AV-fistula mapping.

Alternatively, the volume portion may also be a portion of an article to be inspected non-destructively.

According to a further aspect, the method comprises directly predicting the ultrasound probe motion from the stream of ultrasound images, without the input of any external tracking system, and optionally based on only the image data, i.e., without the input of any sensor data other than the image data.

According to a further aspect, the method is carried out during (i.e., in the context of) acquisition of an ultrasound image of a volume portion by the ultrasound probe. This includes evaluation of previously acquired and stored image data. Preferably, the method (and in particular the determining step) is carried out while the ultrasound data is being acquired, in an at least partially overlapping manner.

According to a further aspect, and apparatus for determining a three-dimensional motion of a movable ultrasound probe 10 during acquisition of an ultrasound image of a volume portion by the ultrasound probe is provided. The apparatus comprises a probe input interface for receiving a stream of ultrasound image data 20 from the ultrasound probe 10 while the ultrasound probe is moved along the volume portion; and a machine-learning module 50. The machine-learning module 50 has an input section adapted for receiving, as an input, at least a sub-set of the ultrasound image data 20, 40 representing a plurality of ultrasound image frames 22, and a training memory section containing a training memory having been trained to determine the relative three-dimensional motion between ultrasound image frames. These parts can be provided by software or by hardware or by a combination of software and hardware. The machine-learning module 50 is adapted for determining, from the input and using the training memory, a three-dimensional motion indicator indicating the relative three-dimensional motion between the ultrasound image frames.

According to a further aspect, the apparatus described herein and in particular the machine-learning module 50 are adapted for carrying out the methods according to any of the embodiments and aspects described herein. Thus, the apparatus may have apparatus parts (modules) for performing each method step described herein. These method steps may be performed by way of hardware components, a computer programmed by appropriate software, by any combination of the two or in any other manner. Thus, in particular, the apparatus comprises a probe input interface for receiving a stream of ultrasound image data 20 from the ultrasound probe 10 while the ultrasound probe is moved along the volume portion. The apparatus further comprises a machine-learning module 50 having an input section adapted for receiving, as an input, at least a sub-set of the ultrasound image data 20, 40 representing a plurality of ultrasound image frames 22, a training memory section containing a training memory having been trained to determine the relative three-dimensional motion between ultrasound image frames. Thereby, the machine-learning module 50 is adapted for determining, from the input and using the training memory, a three-dimensional motion indicator indicating the relative three-dimensional motion between the ultrasound image frames.

REFERENCE SIGNS 2 volume portion/body portion
10 ultrasound probe
11 ultrasound system
12 motion of ultrasound probe 14 sensor
20 ultrasound image data
22 imaging region (image plane) of image frames
24 sensor data
30 (image data) pre-processing module
34 (sensor data) pre-processing module
40 pre-processed ultrasound image data
44 pre-processed sensor data
50 machine learning module
52 training data
60 motion indicator
70 post-processing module
80 post-processed trajectory data
82 determined spatial arrangement of image frames
$I_1, I_2, \ldots I_N$ image frames
$C_1, C_2, \ldots C_N$ determined spatial arrangement of image frame coordinate systems
$M_{12}$ coordinate transformation function for image frame coordinate systems

The invention claimed is:

1. A method of determining a three-dimensional motion of a movable ultrasound probe during acquisition of an ultrasound image of a volume portion by the ultrasound probe, the method comprising:
Receiving a stream of ultrasound image data from the ultrasound probe while the ultrasound probe is moved along the volume portion;
Inputting at least a sub-set of the ultrasound image data representing a plurality of ultrasound image frames into a machine-learning module, wherein the machine learning module has been trained to determine the relative three-dimensional motion between ultrasound image frames; and
Inputting further sensor data into the machine-learning module, wherein the further sensor data is synchronized with the ultrasound image data, and wherein the further sensor data includes at least one of position data, obtained by a tracking system tracking a position of the ultrasound probe, acceleration data representing the acceleration corresponding to the at least two ultrasound image frames, the acceleration being detected by an acceleration sensor attached to the ultrasound probe and gyroscope data; and
Determining, by the machine-learning module, a three-dimensional motion indicator indicating the relative three-dimensional motion between the ultrasound image frames.

2. The method according to claim 1, further comprising pre-processing the ultrasound image data, the pre-processing including at least one of an image filtering, image resampling and image segmentation.

3. The method according to claim 1, wherein the machine learning module comprises a neural network, preferably a convolutional neural network.

4. The method according to claim 1, wherein
the step of inputting the at least sub-set of the ultrasound image data includes inputting local image data corresponding to a pair of ultrasound image frames to the machine learning module, and wherein
the three-dimensional motion indicator indicates the relative three-dimensional motion between the pair of ultrasound image frames, and wherein
the inputting and determining steps are repeated for consecutive pairs or subsets of image frames.

5. The method according to claim 1, wherein
the step of inputting the at least sub-set of the ultrasound image data includes inputting a global set of image data substantially spanning the whole set of ultrasound image frames to the machine learning module, and wherein
the three-dimensional motion indicator indicates the relative three-dimensional motion for determining the relative three-dimensional motion of each of the ultrasound image frames with respect to a first one of the ultrasound image frames.

6. The method according to claim 1, wherein the ultrasound image data includes at least one of A-Mode data, B-Mode data, continuous harmonic imaging data, Doppler data, plain wave imaging data, and raw radio frequency data.

7. The method according to claim 1, further comprising determining, from the three-dimensional motion indicator, a probe position and orientation of the ultrasound probe for each image frame.

8. The method according to claim 7, further comprising tracking the position of the movable ultrasound probe by a further tracking system thereby generating a tracked position information, detecting whether the tracking system fails, and if the tracking system is determined to fail, substituting the tracked position information by the probe position and orientation determined from the three-dimensional motion indicator.

9. The method according to claim 7, further comprising reconstructing a three-dimensional ultrasound image using the stream of ultrasound image data and the probe position and orientation determined from the three-dimensional motion indicator.

10. The method according to claim 1, wherein the method comprises directly predicting the ultrasound probe motion from the stream of ultrasound images using the three-dimensional motion indicator, without using a further tracking system.

11. The method according to claim 1, further comprising detecting an inconsistency between the determined three-dimensional motion indicator and the sensor data.

12. The method according to claim 1, wherein the further sensor data is obtained from an IMU sensor.

13. An apparatus for determining a three-dimensional motion of a movable ultrasound probe during acquisition of an ultrasound image of a volume portion by the ultrasound probe, the apparatus comprising:
a probe input interface for receiving a stream of ultrasound image data from the ultrasound probe while the ultrasound probe is moved along the volume portion; and
a machine-learning module having
(a) an input section adapted for receiving, as an input, at least a sub-set of the ultrasound image data representing a plurality of ultrasound image frames, wherein the input section is characterized in that the input section is adapted for further receiving, as an input, sensor data, wherein the sensor data is synchronized with the ultrasound image data and wherein the sensor data includes at least one of position data, obtained by a tracking system tracking a position of the ultrasound probe, acceleration data representing the acceleration corresponding to the at least two ultrasound image frames, the acceleration being detected by an acceleration sensor attached to the ultrasound probe and gyroscope data,
(b) a training memory section containing a training memory having been trained to determine the relative three-dimensional motion between ultrasound image frames, wherein the machine-learning module is adapted for determining, from the input and using the training memory, a three-dimensional motion indicator indicating the relative three-dimensional motion between the ultrasound image frames.

* * * * *